United States Patent [19]

Amimoto et al.

[11] 4,379,901
[45] Apr. 12, 1983

[54] POLYFLUOROALLYL ETHERS AND THEIR PRODUCTION AND USE

[75] Inventors: Yoshio Amimoto, Takatsuki; Masayoshi Tatemoto, Ibaraki, both of Japan

[73] Assignee: Daikin Kogyo Co., Ltd., Osaka, Japan

[21] Appl. No.: 306,352

[22] Filed: Sep. 28, 1981

[30] Foreign Application Priority Data

Sep. 30, 1980 [JP] Japan ................................ 55-136932

[51] Int. Cl.$^3$ ...................... C07C 121/34; C08F 16/24
[52] U.S. Cl. ................................... 526/247; 260/465.6
[58] Field of Search ....................... 260/465.6; 526/247

[56] References Cited

U.S. PATENT DOCUMENTS 3,641,104 2/1972 Anderson et al. ............... 260/465.6
3,933,767 1/1976 Nottke ................................. 526/247
4,273,728 6/1981 Krespan ........................... 260/465.6

Primary Examiner—Harry Wong, Jr.
Attorney, Agent, or Firm—Birch, Stewart, Kolasch & Birch

[57] ABSTRACT

A polyfluoroallyl ether of the formula:

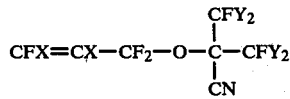

wherein each X, which is the same or different, is a chlorine atom or a fluorine atom and each Y, which is the same or different, is a hydrogen atom, a chlorine atom or a fluorine atom, which is useful as a modifier for polymers.

21 Claims, No Drawings

POLYFLUOROALLYL ETHERS AND THEIR PRODUCTION AND USE

The present invention relates to novel polyfluoroallyl ethers and their production and use.

There are already known various polyfluoroallyl ethers and their polymers, for example, as shown in Japanese Patent Publication (unexamined) No. 82713/1978.

The present invention provides novel polyfluoroallyl ethers characteristic in having a cyano group in the molecule, and their polymers with other monomers copolymerizable with them.

The polyfluoroallyl ethers of the present invention are representable by the formula:

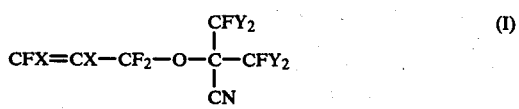

wherein each X, which is the same or different, is a chlorine atom or a fluorine atom and each Y, which is the same or different, is a hydrogen atom, a chlorine atom or a fluorine atom.

The polyfluoroallyl ethers (I) are, in general, colorless, stable liquids under atmospheric conditions. Specific examples are perfluoro(4-oxa-5-cyano-5-methyl-1-hexene), 4-oxa-5-cyano-5-trifluoromethyl-1-chloro-1,2,3,3,6,6,6-heptafluoro-1-hexene, 4-oxa-5-cyano-5-trifluoromethyl-2-chloro-1,1,3,3,6,6,6-heptafluoro-1-hexene, 4-oxa-5-cyano-5-trifluoromethyl-1,2-dichloro-1,3,3,6,6,6-hexafluoro-1-hexene, etc.

The polyfluoroallyl ether (I) may be produced by reacting the corresponding fluoroketone cyanohydrin salt of the formula:

wherein M is an alkali metal and Ys are as defined above with a fluoropropenyl halide of the formula:

$$CFX=CX-CF_2-Z \quad (III)$$

wherein Z is a halogen atom except fluorine and each X is as defined above, preferably in an aprotic solvent.

The starting fluoroketone cyanohydrin salt (II) may be prepared, for example, by reacting the corresponding fluoroketone of the formula:

wherein each Y is as defined above with an alkali metal cyanide in tetrahydrofuran as described in T. Mill et al.: J. Org. Chem., 29, 3715 (1964). The reaction system is preferred to be anhydrous, because the reaction mixture comprising the produced fluoroketone cyanohydrin salt (II) is normally employed as such in the reaction with the fluoropropenyl halide (III), which is desired to be effected under an anhydrous condition. Since the fluoroketone cyanohydrin salt (II) is stable, it may be once isolated from the reaction mixture and then used for the reaction with the fluoropropenyl halide (III).

As stated above, the reaction between the fluoroketone cyanohydrin salt (II) and the fluoropropenyl halide (III) is preferably carried out in an aprotic solvent. Examples of the aprotic solvent are tetrahydrofuran, dioxane, glyme, diglyme, triglyme, dimethylformamide, dimethylacetamide, acetonitrile, sulfolane, nitrobenzene, benzonitrile, etc.

Any particular limitation is not present on the reaction temperature, and usually a temperature between the melting point and the boiling point of the aprotic solvent, especially around a room temperature, is adopted. The reaction time is preferred to be not more than about 20 hours, since when it is longer, by-production of a high boiling compound is increased. The reaction system is preferred to be kept in an anhydrous state.

The polyfluoroallyl ether (I) can be by itself oligomerized. In general, however, it is polymerized with at least one of ethylenically unsaturated monomers to produce a polymer having a cyano group, which is readily convertible into any other group such as carboxyl. Thus, the polyfluoroallyl ether (I) is useful as a modifier, particularly a cyano group-introducing modifier, for polymers.

For preparation of modified polymers, the polyfluoroallyl ether (I) and at least one ethylenically unsaturated monomer are subjected to polymerization in a per se conventional procedure. The ethylenically unsaturated monomer may be any monomer copolymerizable with the polyfluoroallyl ether (I), and its specific examples are ethylene, propylene, vinyl chloride, vinylidene chloride, acrylic acid, methacrylic acid, tetrafluoroethylene, trifluoroethylene, vinylidene fluoride, vinyl fluoride, hexafluoropropylene, chlorotrifluoroethylene, perfluoro(methyl vinyl ether), perfluoro(propyl vinyl ether), etc. Among them, fluorine-containing monomers are preferred from the viewpoint of the effective utilization of the characteristic properties of the polyfluoroallyl ether (I), which also contains a fluorine atom.

The polymerization mode may be any conventional one such as bulk polymerization, solution polymerization, suspension polymerization or emulsion polymerization. In order to carry out the polymerization efficiently, there is usually employed any inert solvent such as trichlorotrifluoroethane, dichlorotetrafluoroethane, trichlorofluoromethane, dichlorodifluoromethane, perfluorocyclobutane or water. As the polymerization initiator, there may be used any conventional one insofar as the properties of the produced polymer are not deteriorated. Specific examples are di(fluoroacyl)peroxides, di(chlorofluoroacyl)peroxides, dialkyl peroxydicarbonates (e.g. diisopropyl peroxydicarbonate), diacylperoxides (e.g. isobutyryl peroxide), peroxyesters (e.g. t-butyl peroxyisobutyrate, t-butyl peroxypivalate), etc. When desired, a chain transfer agent as conventionally employed in radical polymerization (e.g. isoparaffin, tetrachloromethane, dimethyl malonate, diethyl ether, mercaptans, alcohols) may be used. The polymerization temperature is not limited and may be usually from room temperature to 100° C. The polymerization pressure may be autogenic or an elevated one.

The thus produced polymer may comprise units of the polyfluoroallyl ether (I) in any content. From the viewpoint of the properties of the polymer and the economic production of such polymer, however, the content is preferred to be from 0.1 to 50 mol %.

The polymer of the invention can be molded by a per se conventional molding procedure into an appropriate shape. Thus, it is useful as a shaped article. Also, the polymer may be used as an adhesive agent due to the characteristic property of the cyano group present therein. Since the cyano group is an effective vulcanizing site, the polymer may be heated in the presence of a catalyst such as tetraphenyl tin for crosslinking, whereby the physical properties can be modified. Further, the polymer may be treated with conc. alkali for hydrolysis of the cyano group to carboxyl. The resulting product is useful as an ion-exchanger.

Practical and presently preferred embodiments of the invention are illustratively shown in the following Examples.

EXAMPLE 1

Perfluoro(4-oxa-5-cyano-5-methyl-1-hexene):

A mixture of hexafluoroacetone (hereinafter referred to as "HFA") (8.79 g) and potassium cyanide (2.51 g) in diglyme (20 ml) was stirred at room temperature for 4 days. To the reaction mixture, 3-chloropentafluoropropene (hereinafter referred to as "CPFP") (6.68 g) was added, and stirring was effected at a room temperature for 3 hours. The reaction mixture was fractionally distilled to give perfluoro(4-oxa-5-cyano-5-methyl-1-hexene). B.P., 83°–84° C. Yield, 32%.

Elemental analysis. Calcd.: C, 26.0%; N, 4.33%. Found: C, 25.3%; N, 4.17%.

IR spectrum (cm$^{-1}$): 2280 (C≡N), 1790 (C=C), 1300–1100 (C—F), 990 (CF$_2$—O—C).

Mass spectrum: 323 (M$^+$), 304 (M—F)$^+$, 276 (a peak of a metastable ion with 323 appeared at 236), 131 (CF$_2$=CF—CF$_2^+$). $^{19}$F-NMR:

$$\begin{array}{c} \overset{F}{\underset{F}{\phantom{|}}} \overset{3}{\diagdown} \overset{F}{\underset{|}{C}} = \overset{5}{\underset{|}{C}} - CF_2 - O - \underset{\underset{2}{CN}}{\overset{|}{\underset{|}{C}}} - (CF_3)_2 \\ 4 \qquad 1 \end{array}$$

| Chemical shift(*1) (ppm) | Coupling constant(*2) (Hz) | |
| --- | --- | --- |
| +7.3 | doublet of J$_{14}$ multiplet | 23.6 |
| +1.8 | triplet J$_{12}$ | 4.7 |
| −15.1 | doublet of J$_{34}$ | 53.6 |
| | doublet of J$_{35}$ | 41.5 |
| | triplet J$_{31}$ | 7.6 |
| −28.2 | doublet of J$_{45}$ | 118.9 |
| | doublet of J$_{43}$ | 53.6 |
| | triplet J$_{41}$ | 23.6 |
| −114.8 | doublet of J$_{54}$ | 118.9 |
| | doublet of J$_{53}$ | 41.5 |
| | triplet J$_{51}$ | 8.8 |

Notes:
(*1)The lower magnetic field side in comparison with trifluroacetic acid is positive and the higher side is negative.
(*2)Apparent coupling constant.

As a by-product, there was obtained a disubstituted compound, i.e. (CF$_3$)$_2$(CN)COCF=CFCF$_2$OC(CN)(CF$_3$)$_2$ (hereinafter referred to as "the high boiling product"). Yield, 1.7%.

EXAMPLE 2

In the same manner as in Example 1, HFA (20.27 g) and potassium cyanide (7.21 g) were reacted at room temperature for 18 hours. To the reaction mixture, CPFP (20.52 g) was added, and stirring was effected at room temperature for 1 hour. As the result, there were obtained perfluoro(4-oxa-5-cyano-5-methyl-1-hexene) in a yield of 21.8% and the high boiling product in trace.

EXAMPLE 3

The same operations as in Example 1 except that the reaction after the addition of CPFP was continued for 21 hours were carried out to give perfluoro(4-oxa-5-cyano-5-methyl-1-hexene) in a yield of 8.7% and the high boiling product in a yield of 16.6%.

EXAMPLE 4

Copolymer of perfluoro(4-oxa-5-cyano-5-methyl-1-hexene) and tetrafluoroethylene:

In a 100 ml volume stainless steel made autoclave, perfluoro(4-oxa-5-cyano-5-methyl-1-hexene) (1.80 g) and tetrafluoroethylene (5.0 g) were polymerized in the presence of [H(C$_6$F$_{12}$)CO]$_2$O$_2$ as an initiator and trichlorotrifluoroethane (10 ml) as a solvent at 25° C. under an autogenic pressure for 40 hours. Volatile components were eliminated from the reaction mixture to give perfluoro(4-oxa-5-cyano-5-methyl-1-hexene)/tetrafluoroethylene copolymer as a white solid (1.20 g). M.P., 323° C. IR spectrum (cm$^{-1}$): 990 (CF$_2$—O—C). Perfluoro(4-oxa-5-cyano-5-methyl-1-hexene) content, 46 mol % (calculated from the IR absorbance ratio of the IR absorbance based on CF$_2$—C—O and that based on CF$_2$=CF$_2$).

A film formed from the said white solid was heated in 5 N NaOH under reflux for 18 hours. The IR spectrum of the resulting film showed a characteristic band at 1650 cm$^{-1}$ (—COO$^-$), whereby the conversion of the cyano groups into carboxyl was confirmed.

EXAMPLE 5

Terpolymer of perfluoro(4-oxa-5-cyano-5-methyl-1-hexene), vinylidene fluoride and hexafluoropropene:

Into a 3000 ml volume stainless steel made autoclave, purified water (1500 ml) and Na$_2$HPO$_4$.12H$_2$O (7.5 g) were charged, and the interior was thoroughly substituted with hexafluoropropene. Then, perfluoro(4-oxa-5-cyano-5-methyl-1-hexene) (10 g) was added thereto, and a mixture of vinylidene fluoride and hexafluoropropene in a molar ratio of 1:1 was introduced therein while stirring at 80° C. to make a pressure of 12 Kg/cm$^2$ G. Immediately after a 5% aqueous solution of ammonium persulfate (50 ml) was added, the polymerization was initiated. The polymerization was continued for 3.5 hours, during which a mixture of vinylidene fluoride, hexafluoropropene and perfluoro(4-oxa-5-cyano-5-methyl-1-hexene) in a molar ratio of 78:21:1 was supplied therein to maintain the pressure constant. After consumption of 4.2 mol of the mixture, the pressure was lowered. The obtained white aqueous dispersion was diluted with twice volume of water, and a 1% aqueous solution of potash alum was added thereto while stirring. The precipitated substance was collected, washed and dried to give perfluoro(4-oxa-5-cyano-5-methyl-1-hexene)/vinylidene fluoride/hexafluoropropene terpolymer as a gum (355 g).

The intrinsic viscosity [η] of the gum in tetrahydrofuran at 35° C. was 0.72. In the IR spectrum determined on a film formed with the tetrahydrofuran solution on a salt plate, a peak attributable to the allyl ether structure (CF$_2$—O—C) was recognized slightly at 990 cm$^{-1}$.

The gum can be readily vulcanized with hexamethylenediamine carbamate. When heated in the presence of tetraphenyl tin at 200° C., it forms a gel.

What is claimed is:

1. A polyfluoroallyl ether of the formula:

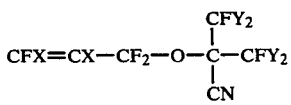

wherein each X, which is the same or different, is a chlorine atom or a fluorine atom and wherein each Y, which is the same or different, is a hydrogen atom, a chlorine atom or a fluorine atom.

2. The polyfluoroallyl ether according to claim 1, wherein each Y is a fluorine atom.

3. The polyfloroallyl ether according to claim 1 or claim 2, wherein each X is a fluorine atom.

4. The polyfluoroallyl ether according to claim 1 or claim 2, wherein one X is a fluorine atom, and the other is a chlorine atom.

5. The polyfluoroallyl ether according to claim 1 or claim 2, wherein each X is a chlorine atom.

6. A process for preparing polyfluoroallyl ethers of the formula:

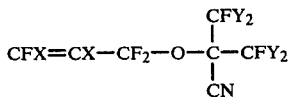

wherein each X, which is the same or different, is a chlorine atom or a fluorine atom and wherein each Y, which is the same or different, is a hydrogen atom, a chlorine atom or a fluorine atom, which comprises reacting a fluoroketone cyanohydrin salt of the formula:

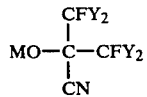

wherein M is an alkali metal and each Y is as defined above with a fluoropropenyl halide of the formula:

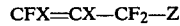

wherein Z is a halogen atom except fluorine and each X is as defined above.

7. The process according to claim 6, wherein the reaction is carried out in an aprotic solvent.

8. The process according to claim 7, wherein the reaction is effected at a temperature wherein said aprotic solvent is in a liquid state.

9. A polymer of a polyfluoroallyl ether comprising units of the formula:

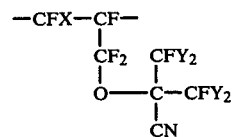

wherein each X, which is the same or different, is a chlorine atom or a fluorine atom and each Y, which is the same or different, is a hydrogen atom, a chlorine atom or a fluorine atom.

10. The polymer according to claim 9, wherein said polymer is a polymer produced by polymerizing a polyfluoroallyl ether of the formula:

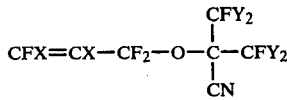

wherein X and Y are the same as defined in claim 9 with at least one other ethylenically unsaturated monomer.

11. The polymer according to claim 9, wherein said polymer is a copolymer produced by polymerizing a polyfluoroallyl ether of the formula:

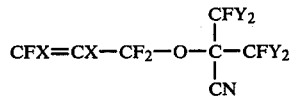

wherein X and Y are the same as defined in claim 9, with one other ethylenically unsaturated monomer.

12. The polymer according to claim 9, wherein said polymer is a terpolymer produced by polymerizing a polyfluoroallyl ether of the formula:

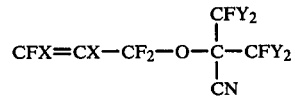

wherein X and Y are the same as defined in claim 11, with two other ethylenically unsaturated monomers.

13. The polymer according to claim 9, wherein the content of the units of the polyfluoroallyl ether is from 0.1 to 50 mol %.

14. The polymer according to claim 10, wherein the content of the units of the polyfluoroallyl ether is from 0.1 to 50 mol %.

15. The polymer according to claim 11, wherein the content of the units of the polyfluoroallyl ether is from 0.1 to 50 mol %.

16. The polymer according to claim 12, wherein the content of the units of the polyfluoroallyl ether is from 0.1 to 50 mol %.

17. The polymer according to claim 10, wherein said at least one other ethylenically unsaturated monomer is a fluorine-containing monomer.

18. The polymer according to claim 10, wherein said at least one other ethylenically unsaturated monomer is a monomer selected from the group consisting of ethylene, propylene, vinyl chloride, vinylidene chloride, acrylic acid, methacrylic acid, tetrafluoroethylene, trifluoroethylene, vinylidene fluoride, vinyl fluoride, hexafluoropropylene, chlorotrifluoroethylene, perfluoro(methyl vinyl ether) and perfluoro(propyl vinyl ether).

19. The copolymer according to claim 11, wherein said one other ethylenically unsaturated monomer is tetrafluoroethylene.

20. The polymer according to claim 12, wherein said two other ethylenically unsaturated monomers are vinylidene fluoride and hexafluoropropene.

21. The polymer according to claim 9, wherein the cyano groups are converted into carboxyl groups.

* * * * *